United States Patent [19]

Huebner

[11] 4,329,348

[45] May 11, 1982

[54] N-OXACYCLIC-ALKYLPIPERIDINES AS PSYCHOSTIMULANTS

[75] Inventor: Charles F. Huebner, Chatham, N.J.

[73] Assignee: Ciba-Geigy Corporation, Ardsley, N.Y.

[21] Appl. No.: 186,776

[22] Filed: Sep. 12, 1980

Related U.S. Application Data

[63] Continuation-in-part of Ser. No. 15,539, Feb. 26, 1979, abandoned, which is a continuation-in-part of Ser. No. 888,089, Mar. 20, 1978, abandoned.

[51] Int. Cl.³ ............... A61K 31/505; A61K 31/445; C07D 405/14
[52] U.S. Cl. ................... 424/251; 424/267; 544/316; 544/332; 546/197; 546/199; 546/210; 546/270
[58] Field of Search ............ 546/199, 197, 202; 544/316, 332; 424/267, 251

[56] References Cited

U.S. PATENT DOCUMENTS

| | | | |
|---|---|---|---|
| 3,513,239 | 5/1970 | Willey et al. ............... | 260/346.73 |
| 3,629,267 | 12/1971 | Kaiser et al. ............... | 546/199 X |
| 3,869,463 | 3/1975 | Archibald .................. | 546/201 |
| 3,910,930 | 10/1975 | Janssen et al. ............. | 546/199 |
| 3,929,801 | 12/1975 | Janssen et al. ............. | 546/199 |
| 4,073,911 | 2/1978 | Huebner .................... | 546/196 X |
| 4,147,786 | 4/1979 | Huebner .................... | 544/316 X |
| 4,235,915 | 11/1980 | Archibald et al. ........... | 546/197 X |

FOREIGN PATENT DOCUMENTS

| | | |
|---|---|---|
| 4358 | 10/1979 | European Pat. Off. . |
| 2852945 | 6/1980 | Fed. Rep. of Germany . |
| 142341 | 6/1980 | German Democratic Rep. . |
| 1404003 | 8/1975 | United Kingdom ............... 546/201 |

*Primary Examiner*—Richard A. Schwartz
*Attorney, Agent, or Firm*—Norbert Gruenfeld; Prabodh I. Almaula

[57] ABSTRACT

N-Oxacyclic-alkylpiperidyl-diazacompounds, e.g., those of the formula

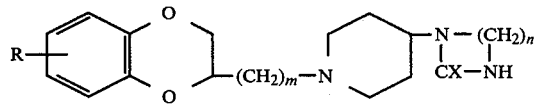

R = H, alkyl, alkoxy, halo or $CF_3$;
X = O, S or NH;
m = 1-4;
n = 2 or 3 and salts thereof are antidepressants and psychostimulants.

8 Claims, No Drawings

N-OXACYCLIC-ALKYLPIPERIDINES AS PSYCHOSTIMULANTS

CROSS-REFERENCE TO RELATED APPLICATION

This is a continuation-in-part of application Ser. No. 015,539, filed Feb. 26, 1979, now abandoned, which in turn is a continuation-in-part of application Ser. No. 888,089, filed Mar. 20, 1978, now abandoned.

SUMMARY OF THE DISCLOSURE

The present invention concerns and has for its object the provision of new N-oxacyclic-alkylpiperidyl-diazacompounds, more particularly of those corresponding to Formula I

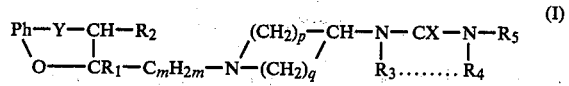

wherein Ph is unsubstituted 1,2-phenylene or 1,2-phenylene substituted by one to three identical or different members selected from lower alkyl; free, etherified or esterified hydroxy or mercapto, such as lower alkoxy, lower alkylenedioxy, benzyloxy, lower alkylmercapto or halogeno; trifluoromethyl; nitro; or amino; each of $R_1$ and $R_2$ is hydrogen or lower alkyl; each of $R_3$ and $R_4$ is hydrogen, lower alkyl or $(R_3+R_4)$ is Ph or lower alkylene separating both nitrogens by 2 to 4 carbon atoms; $R_5$ is hydrogen, lower alkyl, HPh-lower alkyl or HPh; X is oxo, thio, imino or lower alkylimino; Y is epoxy, epithio or sulfinyl; m is an integer from 1 to 7; each of p and q is an integer from 1 to 3, but $(p+q)=4$; the N-oxide of pharmaceutically acceptable acid addition salts thereof; of corresponding pharmaceutical compositions and methods for the preparation and application of these products which are uselful antidepressants and physchostimulants.

DESCRIPTION OF THE PREFERRED EMBODIMENTS

The 1,2-phenylene group Ph is preferably unsubstituted or monosubstituted, and its up to three substituents are illustrated by the following groups: lower alkyl, e.g., methyl, ethyl n- or i-propyl or -butyl; hydroxy; mercapto; lower alkoxy, e.g., methoxy, ethoxy, n- or i-propoxy or -butoxy, lower alkylenedioxy, e.g., methylenedioxy, 1,1- or 1,2-ethylenedioxy; benzyloxy; lower alkylmercapto, e.g., methyl- or ethylmercapto; halogeno, e.g., fluoro, chloro or bromo; trifluoromethyl; nitro or amino. Each of $R_1$ to $R_5$ is preferably hydrogen, but also lower alkyl, advantageously methyl, or another of those mentioned above; $R_5$ may also be phenyl-lower alkyl or phenyl, unsubstituted or substituted as illustrated by H-Ph above; and $(R_3+R_4)$ may also be said 1,2-phenylene Ph or lower alkylene separating both nitrogens by preferably 2 or 3 carbon atoms, e.g., 1,2-ethylene, 1,2- or 1,3-propylene, 1,2-, 1,3- or 2,3-butylene. X is preferably oxo, but also thio, imino or lower alkylimino and Y is preferably epoxy, but also epithio or sulfinyl. Of said integers m is preferably 1 to 4, i.e., $C_mH_{2m}$ advantageously represents methylene, 1,1- or 1,2-ethylene, 1,2- or 1,3-propylene, 1,2-, 1,3- or 1,4-butylene; and each of p and q is preferably 2.

The N-oxide of the compounds of Formula I, which contain no hydrogen attached to basic nitrogen, is derived from the piperidine moiety, i.e. the 1-position thereof. Moreover, all basic compounds of this invention (said N-oxides included) can be in the form of pharmaceutically acceptable acid addition salts, e.g., derived from the acids listed below. As used above and hereinafter in connection with organic radicals or compounds respectively, the term "lower" defines such with up to 7, preferably up to 4, and advantageously 1 or 2 carbon atoms.

The compounds of the invention exhibit valuable pharmacological properties, for example, stimulant and antidepressive effects. This can be demonstrated in animal tests, using advantageously mammals, such as mice, rats or monkeys, as test objects. The compouands of the invention can be applied to the animals enterally, e.g., orally, or parenterally, e.g., subcutaneously, intraperitoneally or intravenously, for example in the form of aqueous solutions or starchy suspensions. The dosage may range between about 0.1 to 100 mg/kg/day, preferably between about 1 and 50 mg/kg/day, especially between about 5 and 25 mg/kg/day. Said stimulant and antidepressive effects can be observed, for example, in male albino rats, which were allowed unrestricted access to food and water, except during experimental sessions. Behavioral testing took place in standard, sound-insulated operant conditioning chambers, which contained a response lever. Electrical shocks were delivered through the grid floor and the chambers were located in small sound-attenuated rooms into which white noise was delivered to mask extraneous auditory cues. The response lever was connected to solid-state programming equipment, which controlled the delivery of the electrical shocks. The number of responses, the response rate and number of shocks received were both recorded on electro-mechanical counters and cumulative recorders. Said rats were first trained to avoid the onset of electrical shock by pressing the lever and about 50% of all rats meet the criterion of less than 100 shocks during a five hour session after about 45 training sessions. Thereafter, the programming equipment was adjusted so that each lever-press postponed the onset of shock for 30 seconds. If the animal failed to press the lever within this time interval, brief electrical shocks were delivered every 15 seconds until the animal again presses the lever. Prior to each test session the rats were placed in the chambers for a fifteen minute warm-up period, during which responding was not recorded. Immediately thereafter the test compounds were given either within saline, or a 3% colloidal corn starch suspension in 5% aqueous polyethyleneglycol 400, containing one drop of polyoxyethylene-20-sorbitan monooleate per 10 ml, administered either orally or intraperitoneally. Thus, for example, the 1-[1-[2-(1,4-benzodioxan-2-yl)-ethyl]-5-piperidyl]-2-imidazolidinone, especially the levorotatory form thereof, e.g., the hydrobromide or fumarate thereof, illustrative of the compounds of Formula I, when orally or intraperitoneally applied at doses as low as 2.5 mg/kg/day, significantly increases the rat's avoidance responding, which compares favorably with 5 mg/kg/day i.p. of methylphenidate (a classical stimulant).

In another test male squirrel monkeys are trained to press a lever in such a Skinner box for avoiding an electric foot shock, applied through the floor grid. Each time a monkey presses the avoidance lever, the shock is postponed for 20 seconds; if it fails to press the lever within said period 0.5 second shocks are delivered at 20 second intervals until the monkey again presses the lever. Under control conditions the monkeys press the lever at a moderately steady rate and seldom receive more than 6 shocks during a four hour session. Measured are the avoidance responses and number of shocks received, being recorded every 15 minutes on both cumulative and response counters. Said hydrobromide or fumarate, when orally administered within 0.9% aqueous sodium chloride, positively changes both the avoidance response rate and number of shocks taken at doses as low as 2.5 mg/kg/day, as compared with a control session (on saline alone) preceding the drug session by one day.

According to other classical tests, the compounds of the invention, e.g., said salts, exhibit a unique mechanism of action. They are apparently not a biogenic amine uptake blocker, an amphetamine-like stimulant prone to abuse liability, not an anticholinergic nor antihistaminic, i.e., free from said common side effects of known antidepressants. They are, therefore, useful psychostimulants, for example in the treatment or management of depression or minimal brain dysfunction (MBD). Moreover, they are also valuable intermediates in the preparation of other useful products, especially of pharmacologically active compositions.

Particularly useful are compounds of Formula I, wherein Ph is 1,2-phenylene unsubstituted or monosubstituted by lower alkyl, hydroxy, mercapto, lower alkoxy, lower alkylenedioxy, benzloxy, lower alkylmercapto, halogeno, trifluoromethyl, nitro or amino; each of $R_1$ and $R_2$ is hydrogen or lower alkyl; each of $R_3$ and $R_4$ is hydrogen, lower alkyl or ($R_3+R_4$) is Ph or lower alkylene separating both nitrogens by 2 or 3 carbon atoms; $R_5$ is hydrogen, lower alkyl, HPh-lower alkyl or HPh; X is oxo, thio, imino or lower alkylimino; Y is epoxy, epithio or sulfinyl, m is an integer from 1 to 4; each of p and q is an integer from 1 to 3, but (p+q)=4; the N-oxide or a pharmaceutically acceptable acid addition salt thereof.

Preferred compounds of the invention are those of Formula I, wherein Ph is 1,2-phenylene unsubstituted or monosubstituted by alkyl or alkoxy with up to 4 carbon atoms each, halogeno or trifluoromethyl; each of $R_1$, $R_2$ and $R_5$ is hydrogen or alkyl with up to 4 carbon atoms; each of $R_3$ and $R_4$ is hydrogen or alkylene with 2 to 4 carbon atoms separating both nitrogens by 2 or 3 carbon atoms; X is oxo, thio or imino, Y is epoxy or epithio, m is an integer from 1 to 4 and each of p and q is the integer 2; the N-oxide or a pharmaceutically acceptable acid addition salt thereof.

Outstanding on account of their antidepressant and stimulant effects are the compounds of Formula II

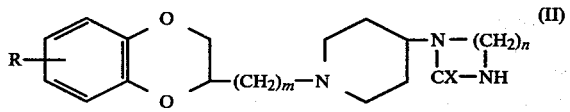

wherein R is hydrogen, alkyl or alkoxy with up to 4 carbon atoms each, halogeno or trifluoromethyl; m is an integer from 1 to 4; n is the integer 2 or 3 and X is oxo, thio or imino; the N-oxide or a pharmaceutically acceptable acid addition salt thereof.

More preferred compounds are those of Formula II, wherein R is hydrogen, methyl, methoxy, fluoro, chloro, bromo or trifluoromethyl, preferably in the 6 to 8 positions; m is an integer from 1 to 4; n is the integer 2 or 3 and X is oxo, thio or imino; the N-oxide or a pharmaceutically acceptable acid addition salt thereof.

The most preferred compounds of this invention are those of Formula II, wherein R is hydrogen, methyl or methoxy in the 6 to 8-positions, m=n=2 and X=O; the N-oxide or a pharmaceutically acceptable acid addition salt thereof.

The compounds of this invention are prepared according to conventional methods, for example by:

(a) condensing reactive esters of oxacyclic alkanols III with 1-unsubstituted piperidyl-diazacompounds IV

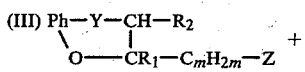

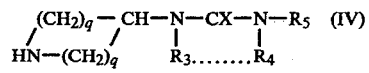

wherein Z is a reactively esterified hydroxy group, for example, such esterified by a strong inorganic or organic acid, above all a hydrohalic acid, e.g., hydrochloric, hydrobromic or hydriodic acid; sulfuric or an aromatic sulfonic acid, e.g., p-toluene or m-bromobenzene sulfonic acid. Said condensation is preferably carried out in the presence of a basic condensation agent, such as an alkali or alkaline earth metal hydroxide, carbonate or bicarbonate, e.g., sodium, potassium or calcium hydroxide or carbonate; alkali metal hydrides, lower alkoxides or alkanoates, e.g., sodium hydride, methylate or acetate, as well as organic tertiary nitrogen bases, such as tri-lower alkylamines or pyridines, e.g. triethylamine or lutidine.

Another process for preparing the compounds of the invention consists in:

(b) reacting N-oxacyclic-alkyl-3 or 4-aminopiperidines V with the carbonic acid derivative VI:

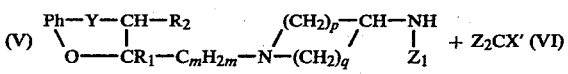

wherein $Z_1$ is $R_3$ or $R_3 \ldots R_4$—NH—$R_5$ and $Z_2CX'$ is an ammonium or metal cyanate or thiocyanate, a lower alkyl isourea or thiourea, a cyanogen halide or amide, carbon disulfide or oxysulfide, a carbonic acid halide or 1,1-carbonyldiimidazole, provided that at least one of $Z_1$ and $Z_2$ contains nitrogen. Said reaction provides either the addition of a carbamoyl group to V if $Z_1=R_3$, or the insertion of CX into V if $Z_1=R_3 \ldots R_4$—N-H—$R_5$. Said cyanate is preferably an alkali metal cyanate, a cyanogen halide advantageously the bromide and the carbonic acid halide preferably phosgene. Said reaction is carried out in the usual manner depending on $Z_2$. In case it is metallic, the reaction is performed in a neutral or acidic solvent or diluent, such as a water-miscible polar solvent, for example an aqueous lower alkanol, alkanone or saturated cyclic ether, e.g. ethanol, acetone, tetrahydrofuran or dioxan, or an alkylated formamide or sulfoxide, e.g. dimethylformamide or -sulfoxide. If $Z_2$ is non-metallic, a basic agent may be used as acid binder, such as an alkali or alkaline earth metal hydroxide, carbonate or bicarbonate, e.g. sodium, potassium or calcium hydroxide or carbonate; alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The compounds of the invention are also obtained by:

(c) reducing N-(oxacyclic terminally oxygenated alkyl)-piperidyldiaza-compounds VII:

$$\begin{array}{c} Ph-Y-CH-R_2 \qquad (CH_2)_p-CH-N-CX-N-R_5 \\ | \qquad | \qquad / \qquad | \qquad | \\ O---CR_1-A-N-(CH_2)_q \qquad R_3........R_4 \end{array} \quad (VII)$$

wherein A is $C_{m-1}H_{2m-2}$—CO ($m \geq 1$) or CO—$C_{m-2}H_{2m-4}$—CO ($m \geq 2$). The reduction is carried out in the usual manner, preferably with the use of simple or complex light metal hydrides, such as diborane or alane, alkali metal boro- or aluminumhydrides or -alkoxyhydrides, e.g. lithium aluminumhydride and/or sodium trimethoxyborohydride. Depending on the presence of ketonic and/or amidic carbonyl in VII, the corresponding alcohols may be formed as intermediates or byproducts, which are further reduced with the use of catalytically activated or nascent hydrogen, such as hydrogen in the presence of cobalt, palladium, platinum or rhodium catalysts, e.g. cobalt sulfide or tris-(triphenylphosphine)rhodium chloride (which are not poisoned by sulfur), or hydrogen generated electrolytically.

Another process for preparing the compounds of the invention consists in:

(d) hydrogenating N-(oxacyclic alkyl or alkenyl)-(piperidyl or tetrahydropyridyl)-diazacompounds VIII;

$$\begin{array}{c} Ph-Y-CH-R_2 \qquad (CH_2)_{\overline{p}}-C_2H_{3-y}-N-CX-N-R_5 \\ | \qquad | \qquad / \qquad | \qquad | \\ O---CR_1-C_mH_{2m-x}-N-(CH_2)_{q-1} \qquad R_3........R_4 \end{array} \quad (VIII)$$

wherein each of x and y is the integer 0 or 2 and their sum x+y is 2 or 4. The hydrogenation of said olefines VIII is performed in the usual manner, preferably with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically.

The compounds of the invention are also obtained by:

(e) ring-closing a reactive ester of an o-hydroxyphenyl-β-hydroxyalkylpiperidyl-diazacompound IX:

$$\begin{array}{c} Ph-Y-CH-R_2 \qquad (CH_2)_p-CH-N-CX-N-R_5 \\ | \qquad | \qquad / \qquad | \qquad | \\ OH \quad Z-CR_1-C_mH_{2m}-N-(CH_2)_q \qquad R_3........R_4 \end{array} \quad (IX)$$

wherein Z is a reactively esterified hydroxy group, for example, such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid. Said ring-closure is preferably carried out in the presence of a basic condensation agent, such as an alkali or alkaline earth metal hydroxide, carbonate or bicarbonate, e.g. sodium, potassium or calcium hydroxide or carbonate; alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The compounds of the invention so obtained can be converted into each other according to known methods. Thus, for example compounds with $R_3$ to $R_5$ being hydrogen, and/or Ph being hydroxy-, mercapto- or amino-1,2-phenylene, or alkali metal, e.g. sodium salts thereof, can be reacted with reactive esters of lower alkanols, alkanediols or benzylalcohol respectively, e.g. such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid, in order to obtain the corresponding N-, O- or S-substituted compounds. Depending on the molar amount of alkylating agent employed, the successive introduction of each $R_3$, $R_4$, and $R_3$ is accomplished. Moreover, said phenols can be etherified with the use of diazoalkanes. Conversely, resulting alkoxy- or benzyloxy-1,2-phenylene compounds may be hydrolyzed, e.g. with strong Lewis acids, such as hydrobromic acid or molten pyridinium chloride. Benzyl ethers may also be cleaved hydrogenolytically, e.g. with the use of catalytically activated or nascent hydrogen, such as hydrogen in the presence of cobalt, palladium, platinum or rhodium catalysts, e.g. cobalt sulfide or tris-(triphenylphosphine)-rhodium chloride (which are not poisoned by sulfur), or hydrogen generated electrolytically. A drastic version of this method may also be employed for dehalogenating Ph, or reducing a nitro group therein to amino. Nitration of Ph may also be carried out in the usual manner, for example, by heating a resulting compound with a mixture of fuming nitric acid and sulfuric acid or acetic anhydride, or a nitrate thereof in trifluoroacetic acid. An iodo atom in Ph may also be replaced by trifluoromethyl, for example by reacting the iodide with trifluoromethyl iodide in the presence of copper powder. Resulting compounds can also be oxidized to the corresponding N-oxides, or compounds with Y=S, to those with Y=SO, with the use of mild or strong oxidants, such as periodates, e.g. sodium periodate in said polar solvents and at low temperature for said sulfinyl compounds; or for said N-oxides with organic peracids, such as lower peralkanoic or perbenzoic acids, e.g. peracetic or m-chloroperbenzoic acid, advantageously at temperatures at or below room temperature, or up to 100° with diluted hydrogen peroxide in the presence of lower alkanoic acids, e.g. acetic acid. Care should be taken, especially with said peracids, in order to prevent overoxidation at overly long reaction times.

Finally, the compounds of the invention are either obtained in the free, basic form, or as a salt thereof. Any resulting base can be converted into a corresponding acid addition salt, preferably with the use of a pharmaceutically useful acid or anion exchange preparation, or resulting salts can be converted into the corresponding free bases, for example, with the use of a stronger base, such as a metal or ammonium hydroxide, basic salt or cation exchange, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material is known or partly new, but can be prepared according to known procedures, e.g. those illustrated in the examples herein.

Compounds of Formula III can easily be obtained by reducing the corresponding 1,4-benzodioxan-2-yl-alkanoic acid to the corresponding alcohol with lithium aluminum hydride or sodium 2-methoxyethoxyaluminum hydride, and reactively esterifying it with a strong acid or its derivative mentioned above, e.g. a thionyl, phosphorus or benzenesulfonyl halide, in an organic solvent, such as benzene, preferably at a raised temperature. Compounds of Formula V are obtained from the previous esters III by condensation with corresponding 3- or 4-benzylaminopiperidines and cleaving the benzyl group by hydrogenation. Compounds VII are prepared from said 1,4-benzodioxan-2-yl-alkanoic acids by converting them into a halide, mixed anhydride or amide of imidazole, and reacting them with the corresponding piperidines. The unsaturated compounds of Formula VIII are preferably enamines prepared from the corresponding aldehydes and said piperidines, and the aldehydes are obtained by reduction of said acid halides according to Rosenmund, or of their nitriles with diisobutylaluminum hydride. Finally the compounds of Formula IX are prepared by the Mannich-reaction of said piperidines with corresponding aldehydes and/or ketones, brominating the resulting piperidinoalkanones, condensing the α-bromoketones obtained with mono-acetylcatechol, reducing the ketonic condensation product with sodium borohydride to the corresponding alcohol and reactively esterifying it as mentioned above.

In case mixtures of geometrical or optical isomers of the above compounds, e.g. I to IX, are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively, and contain about 0.1 to 75%, preferably about 1 to 50%, of the active ingredient.

The following examples are intended to illustrate the invention and are not to be construed as being limitations thereon. Temperatures are given in degrees Centrigrade, and all parts wherever given are parts by weight. If not mentioned otherwise, all evaporations are performed under reduced pressure, preferably between about 15 and 100 mmHg.

EXAMPLE 1

The mixture of 4.9 g of 2-(2-tosyloxyethyl)-1,4-benzodioxan, 2.54 g of 1-(4-piperidyl)-2-imidazolidinone, 5 g of anhydrous sodium carbonate and 100 ml of 4-methyl-2-pentanone is stirred and refluxed for 3 days. It is filtered, evaporated and the residue recrystallized from isopropanol, to yield the 1-[1-[2-(1,4-benzodioxan-2-yl)-ethyl]-4-piperidyl]-2-imidazolidinone of the formula

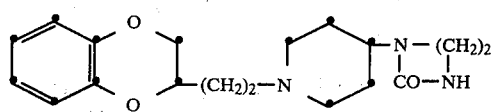

melting at 125°.

It is suspended in 10 ml of hot isopropanol, the suspension neutralized with 5 N isopropanolic hydrogen bromide and the precipitate recrystallized from isopropanol, to yield the corresponding hydrobromide melting at 220–221 with decomposition.

The starting material is prepared as follows: The solution of 16 g of bromine in 10 ml of petroleum ether is slowly added to the solution of 6.7 g of allyl cyanide in 30 ml of the same solvent, while stirring and keeping the temperature at about −15°. After removal of the solvent the oily 3,4-dibromo-butyronitrile is obtained in quantitative yield [J.A.C.S. 67, 400 (1945)].

227 g thereof are added dropwise in 5 equal parts to the stirred mixture of 85 g of catechol and 50 g of anhydrous potassium carbonate in 100 ml of refluxing acetone each. Another 50 g of potassium carbonate are added, followed by a slow addition of another part of nitrile. After 3 more cycles, using 40 g of potassium carbonate, one part nitrile each and sufficient acetone to allow stirring, the mixture is refluxed for 20 hours. It is filtered, the filtrate evaporated, the residue distilled and the fraction boiling at 105°/0.15 mm Hg collected, to yield the 1,4-benzodioxan-2-yl-acetonitrile (Belgium Pat. No. 643,853—Aug. 14, 1964).

The mixture of 111 g thereof, 63.5 ml of sulfuric acid, 160 ml of acetic acid and 160 ml of water is refluxed for 48 hours. It is poured on ice, the resulting solid collected and recrystallized from benzene-petroleum ether, to yield the 1,4-benzodioxan-2-yl-acetic acid melting at 100° (Belgium Pat. No. 613,211—July 30, 1962).

The solution of 5.8 g thereof in 100 ml of benzene is added dropwise to 16.5 ml of a refluxing, 70% benzene solution of sodium bis(2-methoxyethoxy)-aluminum hydride under nitrogen. When addition is complete, the mixture is refluxed for 4 hours, cooled and poured slowly into 20 ml of 25% sulfuric acid. After filtration and removal of the solvent, the residue is taken up in methylene chloride, the solution washed several times with saturated aqueous sodium bicarbonate, dried and evaporated, to yield the oily 2-(2-hydroxyethyl)-1,4-benzodioxan.

The mixture of 3.6 g thereof, 5.7 g of p-toluenesulfonyl chloride and 20 ml of dry pyridine is stirred and cooled in an ice bath for 2 hours. Ice is then added to the mixture, the resulting solid is filtered off and recrystallized from ethyl acetate-petroleum ether, to yield the 2-(2-tosyloxyethyl)-1,4-benzodioxan melting at 82°-3°.

To the solution of 1.6 g of 4-aminopyridine in 7 ml of dimethylformamide 2 g of 2-chloroethylisocyanate are added while stirring and keeping the temperature below 40°. After 2 hours 28 ml of water are added and stirring is continued for 2 hours at room temperature. The precipitate formed is filtered off, washed with water, dried and recrystallized from aqueous ethanol, to yield the 1-(4-pyridyl)-3-(2-chloroethyl)-urea melting at 120°-122°.

To the suspension of 2.66 g thereof in 4 ml of boiling methanol, 2.68 g of 30.8% methanolic sodium methanolate are added while stirring and the mixture is refluxed for 1 hour. It is filtered hot, washed with hot methanol, the filtrate evaporated and the residue is recrystallized from 90% aqeuous ethanol, to yield the 1-(4-pyridyl)-2-imidazolidinone melting at 204°-207°.

The solution of 5 g thereof in 45 ml of water is hydrogenated over 0.8 g of 10% ruthenium on carbon at 120° and 120 atm. until the hydrogen absorption ceases. It is filtered, the filtrate evaporated, the residue taken up in chloroform, the solution dried, evaporated and the residue recrystallized from methylene chloride-petroleum ether, to yield the 1-(4-piperidyl)-2-imidazolidinone melting at 155°-157°.

EXAMPLE 2

The solution of 4.0 g of 1-[1-[2-(p-1,4-benzodioxan-2-yl)-acetyl]-4-piperidyl]-2-imidazolidinone in 50 ml of tetrahydrofuran is added to the cooled and stirred suspension of 1.0 g of lithium aluminum hydride in 100 ml of tetrahydrofuran at 25°. It is stirred at room temperature overnight and decomposed with 10 ml of ethyl acetate, 1.0 ml of water, 2 ml of 15% aqueous sodium hydroxide and 3 ml of water. The mixture is filtered, the filtrate evaporated and the residue dissolved in 25 ml of hot isopropanol. The solution is combined with that of 1.35 g of fumaric acid in 25 ml of hot isopropanol and the precipitate collected after cooling, to yield the p-1-[1-[2-(1,4-benzodioxan-2-yl)-ethyl]-4-piperidyl]-2-imidazolidinone fumarate melting at 210°-213°: $[\alpha]_D = -30.4°$ (methanol).

In the same manner the dextrorotatory salt is obtained, melting at 210°-213°; $[\alpha]_D = +30.8°$ (methanol).

The starting material is prepared as follows: 19.4 g of 1,4-benzodioxan-2-yl-acetic acid and 12.1 g of d-α-methylbenzylamine are dissolved in 100 ml of hot isopropanol. After standing overnight, the salt formed is filtered off and recrystallized five times from isopropanol. Experiments show that this is sufficient to optically resolve said acid. It is liberated with diluted hydrochloric acid, the mixture extracted with diethyl ether and the extract evaporated, to yield the d-1,4-benzodioxan-2-yl-acetic acid with $[\alpha]_D = +49°$ (ethanol).

In like manner, using p-α-methylbenzylamine, the antipode acid is obtained, $[\alpha]_D = -49°$ (ethanol).

The solution of 3.4 g of said p-acid in 60 ml of tetrahydrofuran is stirred with 3.4 g of carbonyldiimidazole for 1 hour. Then 3.05 g of 1-(4-piperidyl)-2-imidazolidinone, suspended in 20 ml tetrahydrofuran, are added and the mixture is stirred overnight. It is evaporated, the residue dissolved in ethyl acetate, the solution washed with N hydrochloric acid and 5% aqueous sodium hydroxide, dried and evaporated, to yield the 1-[1-[2-(p-1,4-benzodioxan-2-yl)-acetyl]-4-piperidyl]-2-imidazolidinone.

EXAMPLE 3

The mixture of 3.34 g of 2-(2-tosyloxyethyl)-1,4-benzodioxan, 1.83 g of 1-(4-piperidyl)-2-hexahydropyrimidinone, 4 g of sodium carbonate and 80 ml of 4-methyl-2-pentanone is refluxed for 3 days. It is filtered hot, the filtrate evaporated and the residue taken up in water. The suspension is made basic with ammonium hydroxide, extracted with chloroform, the extract dried and evaporated. The residue is dissolved in hot ethanol, the solution made acidic with 4.5 N ethanolic hydrogen chloride, cooled and filtered, to yield the 1-[1-[2-(1,4-benzodioxan-2-yl)-ethyl]-4-piperidyl]-2-hexahydropyrimidinone hydrochloride melting at 253°-255°.

Analogously the 1-[1-[2-(1,4-benzodioxan-2-yl)-ethyl]-4-piperidyl]-2-benzimidazolidinone hydrochloride is obtained, melting at 185°-189°.

The starting material is prepared as follows: To the ice cooled stirred solution of 62.5 ml of 1,3-diaminopropane in 100 ml of ethanol, 30 g of 1-benzyl-4-piperidone are added dropwise. The mixture is hydrogenated over 2 g of pre-reduced platinum oxide at 50° and 2.7 atm. for 9 hours. After theoretical hydrogen-uptake the catalyst is filtered off, the filtrate evaporated, the residue distilled and the fraction boiling at 145°-160°/0.2 mmHg collected, to yield the 4-(3-aminopropylamino)-1-benzylpiperidine.

To the stirred, ice-cooled solution of 24.1 g thereof in 100 ml of tetrahydrofuran, 18.3 g of 1,1-carbonyldiimidazole in 250 ml of tetrahydrofuran are added dropwise. After stirring at room temperature for 18 hours the mixture is evaporated, the residue suspended in water, filtered off and recrystallized from ethanol, to yield the 1-(1-benzyl-4-piperidyl)-2-hexahydropyrimidinone melting at 178°–180°.

The solution of 8 g thereof in 100 ml ethanol-acetic acid (1:1) is hydrogenated over 1.5 g 10% palladium on charcoal, at 50° and 2.7 atm. for 4 hours. After filtration through filter cell and removal of the solvent, the residue is taken up in water, the mixture made strongly alkaline with 50% aqueous sodium hydroxide, extracted with chloroform, the extract dried, filtered, evaporated and the residue recrystallized from ethanol, to yield the 1-(4-piperidyl)-2-hexahydropyrimidinone melting at 206°–210°.

The 1-(4-piperidyl)-2-benzimidazolidinone is described in U.S. Pat. No. 3,929,801.

EXAMPLE 4

To the stirred solution of 6 g of 1-[2-(1,4-benzodioxan-2-yl)-ethyl]-4-(2-aminoethylamino)-piperidine in 10 ml of 50% aqueous ethanol, 1.4 ml of carbon disulfide are added dropwise at 25°. The mixture is refluxed for one hour, a drop of concentrated hydrochloric acid is added and refluxing is continued for 5 hours. After cooling overnight the mixture is filtered and the residue washed with ethanol, to yield the 1-[1-[2-(1,4-benzodioxan-2-yl)-ethyl]-4-piperidyl]-2-imidazolidinthione hydrochloride melting at 292°.

The starting material is prepared as follows: The mixture of 10 g of 2-(2-tosyloxyethyl)-1,4-benzodioxan, 10 g of 4-piperidone hydrochloride, 20 g of anhydrous sodium carbonate and 160 ml of dimethylformamide is stirred vigorously at room temperature for 48 hours. It is filtered, the residue washed with a small amount of dimethylformamide and the filtrate evaporated. The residue is dissolved in ethyl acetate, the solution extracted with hydrochloric acid, the extract made alkaline with 50% aqueous sodium hydroxide while cooling and re-extracted with methylene chloride. The latter extract is dried and evaporated, to yield the 2-[2-(4-oxopiperidino)-ethyl]-1,4-benzodioxan, which solidifies on standing.

To the solution of 18 g thereof in 150 ml of ethanol, that of 23 ml of ethylenediamine in 30 ml of ethanol is added and the whole hydrogenated over 2 g of prereduced platinum oxide at 50° and 3 atm. until the requisite amount of hydrogen has been absorbed. The mixture is cooled, filtered and the filtrate evaporated, to yield the 1-[2-(1,4-benzodioxan-2-yl)-ethyl]-4-(2-aminoethylamino)-piperidine as an oil.

EXAMPLE 5

According to the methods illustrated by the preceeding examples, advantageously those indicated in the table below under "Ex.," the following compounds of Formula I are prepared from equivalent amounts of the corresponding starting materials: $R_1=R_2=H$, $R_3+R_4=(CH_2)_2$, $X=O$ and $p=q=2$, (2-position of Ph at Y).

| No. | Ph | Y | m | $R_5$ | Salt | Ex. | m.p. °C. |
|---|---|---|---|---|---|---|---|
| 1 | 1,2-phenylene | O | 1 | H | HCl | 1 | 250–1 |
| 2 | " | O | 3 | H | " | 2 | 280–5 |
| 3 | " | O | 2 | phenyl | " | 1 | 263–5 |
| 4 | 4-CH$_3$—C$_6$H$_3$ | O | 2 | H | " | 1 | 245–6 |
| 5 | 5-CH$_3$—C$_6$H$_3$ | O | 2 | H | " | 1 | 218–0 |
| 6 | 6-CH$_3$O—C$_6$H$_3$ | O | 2 | H | " | 1 | 261–1 |
| 7 | 1,2-phenylene | S | 2 | H | — | 2 | 95–9 |

The various starting materials can be prepared as follows:

The mixture of 10 g of 2-(2-tosyloxyethyl)-1,4-benzodioxan, 2.4 g of sodium cyanide, 4 ml of water and 20 ml of ethanol is refluxed for 48 hours. It is evaporated, the residue taken up in water and extracted with diethyl ether. The extract is dried, evaporated and 5 g of the crude nitrile stirred and refluxed for 48 hours in a mixture of 2.8 ml of sulfuric acid, 7.2 ml of water and 7.2 ml of acetic acid. The mixture is poured into ice water, extracted with diethyl ether, the extract washed with water and re-extracted with aqueous sodium bicarbonate. The alkaline solution is made acidic with hydrochloric acid and extracted with diethyl ether. The extract is dried, evaporated, 2.5 g of the crude acid are dissolved in 25 ml of tetrahydrofuran and the solution treated with 3 g of carbonyldiimidazole for 30 minutes while stirring. 2.4 g of 1-(4-piperidyl)-2-imidazolidinone are added and the mixture is stirred overnight. It is evaporated, the residue dissolved in ethyl acetate, the solution washed with 5% aqueous sodium hydroxide and 5% hydrochloric acid, dried and evaporated, to yield the 1-[1-[3-(1,4-benzodioxan-2-yl)-propionyl]-4-piperidyl]-2-imidazolidinone.

To the solution of 12.6 g of N-phenylethyleneidamine in 200 ml of methanol, 50 ml of 4.1 N ethanolic hydrogen chloride are added dropwise followed by 18.9 g of 1-benzyl-4-piperidone in 100 ml of methanol. Then, 9.45 g sodium cyanoborohydride are added in portions while stirring at room temperature. After 72 hours the mixture is filtered, the residue dissolved in water and the solution made basic with 12.5% aqueous sodium hydroxide. It is extracted with methylene chloride, dried and evaporated to yield the 1-benzyl-4-(2-phenylaminoethylamino)-piperidine.

To the stirred solution of 14 g thereof in 100 ml of dry benzene, 170 ml of 12.5% phosgene in benzene are added dropwise at room temperature. After stirring overnight the gelatinous precipitate is filtered through a sintered glass funnel, the solid dissolved in hot water, the solution made basic with ammonium hydroxide and the precipitate filtered off, to yield the 1-(1-benzyl-4-piperidyl)-3-phenyl-2-imidazolidinone melting at 168°–170°.

The solution of 10 g thereof in 200 ml ethanol-acetic acid (1:1) is hydrogenated over 1 g of 10% palladium on charcoal for 8 hours at 50° and 2.7 atm. After filtration through filter cell and removal of the solvent, the residue is made basic with 25% aqueous sodium hydroxide and the mixture extracted with diethyl ether. The organic layer is dried and evaporated, to yield the 1-(4-piperidyl)-3-phenyl-2-imidazolidinone.

The solution of 48.6 g of 2-(7-methyl-1,4-benzodioxan-2-yl)-acetic acid in the minimum amount of tetrahydrofuran is added dropwise at reflux rate to the stirred suspension of 13.4 g of lithium aluminum hydride in 200 ml of dry tetrahydrofuran. The mixture is refluxed overnight, cooled, and decomposed by the addition of 13.4 ml of water, 13.4 ml 15% aqueous sodium hydroxide and 40 ml of water. It is filtered, evaporated, the residue distilled in a molecular still, and the fraction boiling at 155°–165°/0.1 mmHg collected as colorless oil, to yield the 2-(2-hydroxyethyl)-7-methyl-1,4-benzodioxan.

To the refluxing solution of 75 g of 2-hydroxythiophenol [J. Pharm. Sci. 61, 2 (1972)] in 660 ml of acetone is added 42 g of potassium carbonate, followed by the dropwise addition of the solution of 33.5 g of 3,4- dibromobutyronitrile in 50 ml of acetone while stirring. After 30 minutes refluxing, a second, third, and fourth addition of 42 g potassium carbonate and 33.5 g of 3,4-dibromobutyronitrile is made. The whole mixture is refluxed for 20 hours, cooled and filtered. The filtrate is evaporated and the residue distilled in a bulb to bulb apparatus at 185° and 0.5 mmHg, to yield the 2-(1,4-benzoxathian-2-yl)-acetonitrile.

The mixture of 57 g thereof, 85 ml water, 85 ml acetic acid and 32.6 ml of sulfuric acid is refluxed for 48 hours, cooled poured onto ice and extracted with benzene. The organic phase is extracted with aqueous sodium bicarbonate, the aqueous phase acidified with hydrochloric acid and extracted with diethyl ether. The extract is dried and evaporated, to yield the corresponding carboxylic acid as an oil. Reacting it with carbonyldiimidazole and then with the 1-(4-piperidyl)-2-imidazolidinone as described in Example 2 gives the desired amide.

EXAMPLE 6

To the stirred solution of 6 g of 1-[2-(1,4-benzodioxan-2-yl)-ethyl]-4-(2-aminoethylamino)-piperidine in 15 ml of tetrahydrofuran, that of 1.58 g of cyanogen bromide in 15 ml of tetrahydrofuran is added at 5°. After 2 hours the mixture is filtered, the residue dissolved in the minimum amount of water, the solution made strongly basic with sodium hydroxide and extracted with methylene chloride. The extract is dried, evaporated, the residue taken up in 50 ml of anhydrous ethanol and the solution combined with 0.1 g of sodium methoxide. It is refluxed overnight, evaporated, the residue taken up in water and the mixture extracted with methylene chloride. The extract is dried, evaporated, the residue dissolved in the minimum amount of isopropanol, the solution neutralized with ethereal oxalic acid and the solids collected to yield the 1-[1-[2-(1,4-benzodioxan-2-yl)-ethyl]-4-piperidyl]-2-imino-imidazolidine oxalate melting at 215°–220° with decomposition.

EXAMPLE 7

Preparation of 10,000 tablets each containing 5 mg of the active ingredient:

| Formula: | |
| --- | --- |
| 1-[1-[2-(1,4-benzodioxan-2-yl)-ethyl]-4-piperidyl]-2-imidazolidinone | 50.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

Preparation of 10,000 capsules each containing 2.5 mg of the active ingredient:

| Formula: | |
| --- | --- |
| 1-[1-[2-(1,4-benzodioxan-2-yl)-ethyl]-4-piperidyl]-2-imidazolidinone | 25.0 g |
| Lactose | 1,875.0 g |
| Talcum powder | 100.0 g |

PROCEDURE

All the powders are passed through a screen with openings of 0.6 mm. Then the drug substance is placed in a suitable mixer and mixed first with the talcum, then with the lactose until homogeneous. No. 3 capsules are filled with 200 mg each, using a filling machine.

Analogously tablets and hard gelatin capsules of the other compounds, described in the remaining examples, are prepared.

EXAMPLE 8

To the solution of 2 g of 1-[1-[2-(1,4-benzodioxan-2-yl)-ethyl]-4-piperidyl]-2-imidazolidinone in the minimum amount of ethanol, the saturated solution of 0.78 g of furmaric acid in boiling ethanol is added. The mixture is cooled to 0° and the precipitate collected, to yield the corresponding fumarate melting at 190°.

EXAMPLE 9

To the solution of 3.47 g of 1-[1-[2-(1,4-benzoxathian-2-yl)-ethyl]-4-piperidyl]-2-imidazolidinone (Example 5, No. 8) in 10 ml of dioxane and 10 ml of methanol, the solution of 2.8 g of sodium metaperiodate in 20 ml of water is added dropwise while stirring at room temperature. After 2 hours the mixture is evaporated, the residue taken up in water and the mixture extracted with methylene chloride. The extract is washed with saturated aqueous sodium chloride, dried, evaporated and the residue recrystalized from isopropanol, to yield the 1-[1-[2-(4-oxo-1,4-benzooxathian-2-yl)-ethyl]-4-piperidyl]-2-imidazolidinone; m.p. 145°.

EXAMPLE 10

The mixture of 0.5 g of 1-[1-[3-(1,4-benzodioxan-2-yl)-2-propenyl]-4-piperidyl]-2-imidazolidinone, 25 ml of ethanol acetic acid (1:1) and 0.1 g of 10% palladium on charcoal is hydrogenated at 2.7 atm. and room temperature until one mole equivalent of hydrogen has been absorbed. The catalyst is filtered off, the filtrate evaporated, the residue dissolved in 5 ml of water and the solution made basic with aqueous ammonia. The mixture is extracted with methylene chloride, the extract dried, evaporated and the residue taken up in the minimum amount of isopropanol. The solution is acidified with ethanolic hydrogen chloride and the precipitate collected, to yield the 1-[1-[3-(1,4-benzodioxan-2-yl)-propyl]-4-piperidyl]-2-imidazolidinone hydrochloride melting at 282°–285° with decomposition; it is identical with that obtained according to Example 5, No. 2.

The starting material is prepared as follows:

The mixture of 10 g of 2-(1,4-benzodioxan-2-yl)-oxiran [Tetrahedron 18, 289 (1962)], 2 g of potassium cyanide, 2 g of ammonium chloride and 25 ml of dimethylformamide is stirred at room temperature for 3 days. The mixture is diluted with water and extracted with methylene chloride. The extract is evaporated and the residue dehydrated by refluxing in a mixture of 11 ml of acetic acid, 11 ml of water and 4 ml of sulfuric acid for 24 hours. The mixture is diluted with ice, extracted with diethyl ether and the extract evaporated to yield the 3-(1,4-benzodioxan-2-yl)-acrylic acid. The solution of 5 g thereof in 25 ml of tetrahydrofuran is treated with 5.5 g of carbonyldiimidazole and the mixture, stirred for 30 minutes. Then the solution of 4.6 g of 1-(4-piperidyl)-2-imidazolidinone in 25 ml of iospropanol is added and the mixture allowed to stand overnight. It is evaporated, the residue taken up in ethyl acetate, the solution washed successively with water, diluted aqueous sodium hydroxide and water and evaporated. The residue is dissolved in 100 ml of tetrahydrofuran, cooled in an ice bath and treated dropwise with 20 ml of a 1.2 molar solution of alane triethylamine complex while stirring. After 5 hours, the cold mixture is treated dropwise with 10 ml of 25% aqueous sodium hydroxide, the organic solvent phase is decanted from the pasty slurry of inorganic salts and evaporated to give the 1-[1-[3-(1,4-benzodioxan-2-yl)-2-propenyl]-4-piperidyl]-2-imidazolidinone.

EXAMPLE 11

The mixture of 4.0 g of 2-(2-tosyloxyethyl)-6,7-dichloro-1,4-benzodioxan, 1.69 g of 1-(4-piperidyl)-2-imidazolidinone, 10 g of ahydrous sodium carbonate and 100 ml of 4-methyl-2-pentanone is stirred and refluxed for 2 days. It is filtered, evaporated and the residue recrystallized from acetone, to yield the 1-[1-[2-(6,7-dichloro-1,4-benzodioxan-2-yl)-ethyl]-4-piperidyl]-2-imidazolidinone melting at 165°.

It is suspended in 10 ml of hot ethanol, the suspension neutralized with 5 N ethanolic hydrogen chloride and the precipitate recrystallized from ethanol-diethyl ether, to yield the corresponding hydrochloride melting at 250°.

The starting material is prepared as follows: To the solution of 60 g of catechol in 200 ml of diethyl ether is slowly added 93 g of sulfuryl chloride during 2 hours while stirring and keeping the temperature at about 0°. After standing for 2 days at room temperature, the mixture is evaporated and the residue recrystallized twice from benzene, to yield the 4,5-dichlorocatechol melting at 85°-90°. To 53.4 g thereof are added dropwise 5 equal parts of 89 g of 3,4-dibromobutyronitrile, in the presence of 33 g of anhydrous potassium carbonate and 800 ml of acetone while refluxing and stirring. Another 20 g of potassium carbonate are added, followed by the slow addition of another part of nitrile. After 3 more cycles, using 20 g of potassium carbonate per part of nitrile each, and sufficient acetone to allow stirring, the mixture is refluxed for 20 hours. It is filtered, the filtrate evaporated, the residue taken up in methylene chloride, the solution washed with water, dried and evaporated. The residue is recrystallized from isopropanol with the aid of charcoal, to yield the 6,7-dichloro-4-benzodioxan-2-yl-acetonitrile melting at 110°.

The mixture of 59 g thereof, 24 ml of sulfuric acid, 60 ml of acetic acid and 60 ml of water is refluxed for 48 hours. It is poured on ice, the resulting solid collected and recrystallized from aqueous ethanol, to yield the 6,7-dichloro-1,4-benzodioxan-2-yl-acetic acid melting at 145°-147°.

The solution of 2.63 g thereof in 40 ml of benzenetetrahydrofuran (1:1) is added dropwise to 5.5 ml of a refluxing, 70% benzene solution of sodium bis(2-methoxyethoxy)-aluminum hydride under nitrogen. When the addition is complete, the mixture is refluxed for 2.5 hours, cooled and poured slowly into 6.7 ml of 20% sulfuric acid. After filtration and removal of the solvent, the residue is taken up in methylene chloride, the solution washed several times with saturated aqueous sodium bicarbonate, water and saturated aqueous sodium chloride, dried and evaporated, to yield the oily 2-(2-hydroxyethyl)-6,7-dichloro-1,4-benzodioxan, boiling at 180°-190°/0.1 mm Hg.

The mixture of 15.2 g thereof, 17.5 g of p-toluenesulfonyl chloride and 40 ml of dry pyridine is stirred and cooled in an ice bath for 2 hours. Ice is then added to the mixture, the resulting solid is filtered off and recrystallized from ethyl acetate, to yield the 2-(2-tosyloxyethyl)-6,7-dichloro-1,4-benzodioxan melting at 135°-138°.

EXAMPLE 12

450 g of d-1-[1-[2-(l-1,4-benzodioxan-2-yl)-acetyl]-4-piperidyl]-2-imidazolidinone are added portionwise during 100 minutes to the stirred suspension of 100 g of lithium aluminumhydride in 6,500 ml of tetrahydrofuran at 2°-6°. The mixture is stirred at room temperature for 19 hours, cooled again and 100 ml of water are added during 100 minutes at 8°-12°, followed by 100 ml of 15% aqueous sodium hydroxide and 300 ml of water. The mixture is stirred for 30 minutes in the cold and 90 minutes at room temperature. It is filtered, the residue washed with 2,000 ml of tetrahydrofuran and the filtrate evaporated, to yield the l-l-[1-[2-(1,4-benzodioxan-2-yl)-ethyl]-4-piperidyl]-2-imidazolidinone melting at 119°-122°; $[\alpha]_D^{25} = -47.3°$ (c=1 in methanol).

1,191 g thereof are dissolved in 3,000 ml of 95% aqueous ethanol at 60°, 120 g of charcoal are added and the mixture is stirred for 5 minutes. It is filtered, the residue washed with 200 ml of 95% ethanol and the filtrate combined with the solution of 441 g of fumaric acid in 7,200 ml of 95% ethanol at 60°. The resulting suspension is diluted with 1,000 ml of 95% ethanol and stirred at room temperature for 3 hours. It is filtered, the residue washed with 500 ml of 95% ethanol and 800 ml of anhydrous diethyl ether, to yield the l-l-[1-[2-(1,4-benzodioxan-2-yl)ethyl]-4-piperidyl]-2-imidazolidinone fumarate melting at 216°-217° with decomposition; $[\alpha]_D^{25} = -31.6°$ (13.73 mg/ml in water); it is identical with that obtained according to Example 2.

The starting material is prepared as follows: To the solution of 1,134 g of bromine in 1,400 ml of ethyl acetate 472 g of allyl cyanide are added dropwise while stirring for 90 minutes at −10°-0°. The resulting solution of 3,4-dibromobutyronitrile is added all at once to the solution prepared from 705 g of catechol and 1,987 g of anhydrous potassium carbonate in 5,000 ml of refluxing ethyl acetate, while stirring at 35° under nitrogen. The mixture is refluxed for 4 hours and stirred overnight at room temperature. It is filtered, the residue washed with 2,000 ml of ethyl acetate, the filtrate evaporated, the residue distilled and the fraction boiling at 138°/1.4-131°/1.1 mm Hg collected, to yield the 1,4-benzodioxan-2-yl-acetonitrile.

The solution of 1,647 g thereof in 2,760 ml of glacial acetic acid is added to the hot mixture of 858 ml of concentrated sulfuric acid and 2,670 ml of water and the whole is refluxed for 17 hours. It is poured into 8,200 ml of cold water, stirred for 3 hours, filtered and washed with 9,000 ml of water to yield the 1,4-benzodioxan-2-yl-acetic acid melting at 87°-90°.

To the mixture of 3,374 g thereof and 3,500 ml of anhydrous ethanol the solution of 2,105 g of l-α-methylbenzylamine in 500 ml of anhydrous ethanol is added and the mixture is stirred for 3 hours at room temperature. After standing at 4°-5° for 2 days, the salt formed is filtered off and washed with 400 ml of ethanol, 400 ml of diethyl ether and 1,200 ml of isopropanol. 2,070 g of the residue are recrystallized from 2,000 ml of ethanol and washed with 500 ml of ethanol and diethyl ether each, to yield the l-1,4-benzodioxan-2-yl-acetic acid l-α-methylbenzylammonium salt melting at 132°-133°.

1,827 g thereof are added to 10,000 ml of 1 N hydrochloric acid while stirring for 20 minutes, 6,000 ml of diethyl ether are added and stirring is continued for 20 minutes. The aqueous layer is separated, extracted with 3,000 ml of diethyl ether, the combined ethereal solutions washed with 1,000 ml of water, dried and evaporated, to yield the l-1,4-benzodioxan-2-yl-acetic acid melting at 83°-85°; $[\alpha]^{25} = -55.42°$ (12.32 mg/ml in methanol).

The mixture of 400 g thereof, 2,000 ml of toluene and 320 ml of thionyl chloride is stirred at 80° for 3 hours and evaporated. The residue is taken up in 500 ml of chloroform and the solution again evaporated, to yield the l-1,4-benzodioxan-2-yl-acetyl chloride melting at 60°-62°.

The solution of 434 g thereof in 1,000 ml of chloroform is added during 2 hours to the mixture of 400 g of 1-(4-piperidyl)-2-imidazolidinone, 4,000 ml of chloroform and 2,600 ml of 1 N aqueous sodium carbonate, while stirring at 20°-23°. After 2 hours the organic solution is separated, the aqueous phase extracted with 1,000 ml of chloroform, the combined organic solutions washed with 1,000 ml of water, dried and evaporated. The residue is triturated with 1,000 ml of anhydrous diethyl ether, filtered and the residue washed with another 1,000 ml of diethyl ether, to yield the d-l-[1-[2-(l-1,4-benzodioxan-2-yl-)acetyl]-4-piperidyl]-2-imidazolidinone melting at 161°-163°; $[\alpha]_D^{25} = +5.9°$ (c=1 in chloroform).

EXAMPLE 13

To the stirred solution of 2 g of 1-[2-(1,4-benzodioxan-2-yl)-ethyl]-4-(2-aminoethylamino)-piperidine in 25 ml of isopropanol is added 1.65 ml of 4 N ethanolic hydrogen chloride, followed by 0.45 g of ammonium cyanate. After refluxing overnight, the mixture is evaporated and heated in an oil bath to 130° for 4 hours. The residue is dissolved in 100 ml of methylene chloride, the solution washed with water, dried, evaporated and the residue taken up in 20 ml of hot isopropanol. 0.77 g of fumaric acid are added with stirring, to effect solution, and on cooling, the 1-[1-[2-(1,4-benzodioxan-2-yl)ethyl]-4-piperidyl]-2-imidazolidinone fumarate is obtained, melting at 190°.

EXAMPLE 14

The mixture of 10 g of 1-[2-(1,4-benzodioxan-2-yl)-ethyl]-4-(2-aminoethylamino)-piperidine, 8 g of carbonyldiimidazole and 100 ml of tetrahydrofuran is refluxed overnight and evaporated. The residue is taken up in 150 ml of methylene chloride, the solution washed three times with 50 ml of water each, dried and evaporated. The residue is dissolved in 50 ml of hot isopropanol and 3.8 g of fumaric acid are added while stirring. On cooling the 1-[1-[2-(1,4-benzodioxan-2-yl)-ethyl]-4-piperidyl]-2-imidazolidinone fumarate crystallizes and is collected; m.p. 190°.

EXAMPLE 15

The solution of 10 g of 1-[1-[2-(1,4-benzodioxan-2-yl)-ethyl]-4-(1,2,3,6-tetrahydropyridyl)]-2-imidazolidinone in 100 ml of acetic acid and 50 ml of water is hydrogenated over 1 g of platinum oxide at 3.4 atm. and 60° until the hydrogen uptake ceases. The mixture is cooled to room temperature, filtered, and the filtrate evaporated. The residue is taken up in 100 ml of water, the mixture adjusted with 3 N aqueous sodium hydroxide to pH=10 and extracted with 100 ml of methylene chloride. The extract is washed with water, dried, evaporated and the residue taken up in 50 ml of hot isopropanol. The solution is acidified with fumaric acid while stirring until solution occurs. On cooling, the 1-[1-[2-(1,4-benzodioxan-2-yl)-ethyl]-4-piperidyl]-2-imidazolidinone fumarate crystallizes; m.p. 190°, 12 g (83%).

The starting material is prepared as follows: The mixture of 10 g of 2-(2-tosyloxyethyl)-1,4-benzodioxan, 4.9 g of 1-(4-pyridyl)-2-imidazolidinone and 0.3 of potassium iodide is heated at 90° overnight and evaporated under reduced pressure. The residue is dissolved in 500 ml of ethanol and 30 g of sodium borohydride are added in portions over two hours while cooling and stirring. The mixture is concentrated to a small volume, diluted with 100 ml of water and extracted with 200 ml of methylene chloride. The extract is washed with water, dried and evaporated, to yield the 1-[1-[2-(1,4-benzodioxan-2-yl)-ethyl]-4-(1,2,3,6-tetrahydropyridyl)]-2-imidazolidinone, which is used as such without further purification.

EXAMPLE 16

To the solution of 7.8 g of l-l-[1-[2-(1,4-benzodioxan-2-yl)-ethyl]-4-piperidyl]-2-imidazolidinone (Example 12) in 100 ml of methylene chloride, that of 6.5 g of m-chloroperbenzoic acid in 150 ml of methylene chloride is added during 30 minutes while stirring at 0°. After standing overnight at room temperature, the mixture is chromatographed on 200 g of basic alumina, eluted with methylene chloride-methanol (7:3) and the eluate evaporated. The residue is taken up in 20 ml of isopropanol, the solution combined with that 2 ml of methanesulfonic acid in 5 ml of water, and the precipitate formed collected, to yield the l-l-[2-(1,4-benzodioxan-2-yl)-ethyl]-4-(2-oxoimidazolidin-1-yl)-piperidine-1-oxide mesylate dihydrate melting at 90°-94° with dehydration; $[\alpha]_D^{25} = -24.3°$ (2% in water).

It may also be obtained by similar oxidation with 30% hydrogen peroxide in methanol at room temperature, whereby said chromatography can be avoided.

5 g of said residue threrefrom may also be taken up in 25 ml of isopropanol and the solution combined with 2.6 g of cyclohexylsulfamic acid, the precipitate collected and recrystallized from water, to yield the corresponding cyclamate melting at 180° with decomposition.

I claim:

1. A compound of the formula

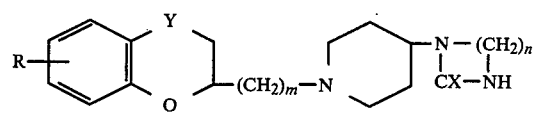

wherein R is hydrogen; m and n are the integer 2 or 3; X is oxo and Y is oxygen or sulfur; the N-oxide or a pharmaceutically acceptable acid addition salt thereof.

2. A compound of claim 1, in which formula R is hydrogen, m=n=2 and X=Y=O; the N-oxide or a pharmaceutically acceptable acid addition salt thereof.

3. A compound of claim 2 being the levorotatory 1-[2-(1,4-benzodioxan-2-yl) ethyl]-4-(2-oxoimidazolidin-1-yl)-piperidine-1-oxide mesylate.

4. A compound as claimed in claim 2 and being 1-[1-[2-(1,4-benzodioxan-2-yl)-ethyl]-4-piperidyl]-2-imidazolidinone or a pharmaceutically useful acid addition salt thereof.

5. A compound as claimed in claim 4, and being in the opticaly levorotatory form thereof.

6. A method for the treatment or management of depression and minimal brain dysfunction, which comprises administering to a mammal, suffering therefrom, enterally or parenterally a pharmaceutical composition comprising an effective amount of a compound of formula I having psychostimulant activity

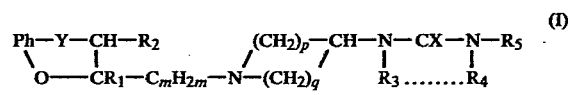

wherein Ph is unsubstituted 1,2-phenylene or 1,2-phenylene substituted by one to three identical or different members selected from lower alkyl, hydroxy, mercapto, lower alkoxy, lower alkylenedioxy, benzyloxy, lower alkylmercapto, halogeno, trifluoromethyl, nitro or amino; each of $R_1$ and $R_2$ is hydrogen or lower alkyl; each of $R_3$ and $R_4$ is hydrogen, lower alkyl or ($R_3+R_4$) is Ph or lower alkylene separating both nitrogens by 2 to 4 carbon atoms; $R_5$ is hydrogen, lower alkyl, HPh-lower alkyl or HPh; X is oxo, thio, imino or lower alkylimino; Y is epoxy, epithio or sulfinyl; m is an integer from 1 to 7; each of p and q is an integer from 1 to 3, but (p+q)=4; the N-oxide or a pharmaceutically acceptable acid addition salt thereof; together with a pharmaceutical excipient.

7. An antidepressant and stimulant pharmaceutical composition comprising an antidepressively effective amount of a compound as claimed in claim 1, together with a pharmaceutical excipient.

8. A method for the treatment or management of depression and minimal brain dysfunction, which comprises administering to a mammal, suffering therefrom, enterally or parenterally a composition as claimed in claim 7.

* * * * *